United States Patent [19]
Castelli

[11] Patent Number: 5,713,365
[45] Date of Patent: Feb. 3, 1998

[54] POCKET INSTRUMENT FOR DETECTING AN ELECTRIC BIOLOGICAL SIGNAL, IN PARTICULAR AN ELECTROCARDIOGRAPHIC SIGNAL

[76] Inventor: Arrigo Castelli, Via Gerso, 3, 6900 Lugano, Switzerland

[21] Appl. No.: 688,960
[22] Filed: Jul. 31, 1996

[30] Foreign Application Priority Data

Aug. 1, 1995 [IT] Italy ................................. TO95A0646

[51] Int. Cl.$^6$ ................................................. A61B 5/04
[52] U.S. Cl. ................................................. 128/696; 128/902
[58] Field of Search ................................. 128/902, 696

[56] References Cited

U.S. PATENT DOCUMENTS

| | | |
|---|---|---|
| 4,191,195 | 3/1980 | Miller . |
| 4,596,256 | 6/1986 | Ascher et al. ............... 128/710 |
| 5,002,062 | 3/1991 | Suzuki ............................. 128/710 |
| 5,392,784 | 2/1995 | Gudaitis ........................... 128/696 |

FOREIGN PATENT DOCUMENTS

| | | | |
|---|---|---|---|
| A 9048187 | 3/1982 | European Pat. Off. . | |
| A 0106756 | 4/1984 | European Pat. Off. | ...... A61B 5/0404 |
| A 0617917 | 10/1994 | European Pat. Off. . | |
| A 4417609 | 2/1995 | Germany . | |

*Primary Examiner*—William E. Kamm
*Assistant Examiner*—Scott Getzow
*Attorney, Agent, or Firm*—Darby & Darby

[57] ABSTRACT

An instrument for detecting an electric biological signal, and wherein a pocket casing housing an electronic circuit presents a rectangular wall fitted with two flat electrodes and a display. The electronic circuit includes an amplifier stage wherein a first operational amplifier communicates at the input with a first electric line receiving a first electric signal picked up from a first portion of the human body, and a second operational amplifier communicates at the input with a second electric line receiving a second electric signal picked up from a second portion of the human body. An inverting amplifier receives a signal equal to the average of the output signals of the first and second operational amplifiers, and is connected at the output to a signal divider for supplying the signal at the output of the inverting amplifier to the first and second electric lines. The user of the instrument grips the casing and places the left and right thumbs on the electrodes to establish electrical connection between the body of the user and the electronic circuit. (FIGS. 1 and 3)

18 Claims, 3 Drawing Sheets

POCKET INSTRUMENT FOR DETECTING AN ELECTRIC BIOLOGICAL SIGNAL, IN PARTICULAR AN ELECTROCARDIOGRAPHIC SIGNAL

BACKGROUND OF THE INVENTION

The present invention relates to a pocket instrument for detecting an electric biological signal, in particular an electrocardiographic signal.

Instruments for detecting electrocardiographic signals are known to feature amplifying circuits comprising a first amplifier communicating at the input with a first electrode for receiving an electric signal picked up from a first portion of the human body (e.g. the right arm), a second amplifier communicating at the input with a second electrode for receiving an electric signal picked up from a second portion of the human body (e.g. the left arm), and a third inverting amplifier for amplifying the difference between the output signals of the first and second amplifiers, and communicating at the output with a third electrode applied to a third portion of the human body (e.g. a leg). The first and second electrodes pick up electric biological body signals generated by the action of the heart, while the third supplies a feedback signal for eliminating (or at least attenuating) noise signals present in the human body, and which are typically periodic signals caused by line voltage.

To operate correctly, such instruments therefore require three external electrodes located at different parts of the body.

SUMMARY OF THE INVENTION

It is an object of the present invention to provide a two-electrode pocket instrument with an amplifying circuit of the aforementioned type, for detecting, processing and displaying an electric biological signal, in particular an electrocardiographic signal. It is a further object of the present invention to provide for straightforward, rapid electric connection of the human body and the electrodes, with a high degree of noise rejection.

According to the present invention, there is provided a pocket instrument for detecting an electric biological signal, in particular an electrocardiographic signal, as claimed in Claim 1.

BRIEF DESCRIPTION OF THE DRAWINGS

A preferred, non-limiting embodiment of the present invention will be described by way of example with reference to the accompanying drawings, in which.

DETAILED DESCRIPTION OF THE INVENTION

Figure 1:
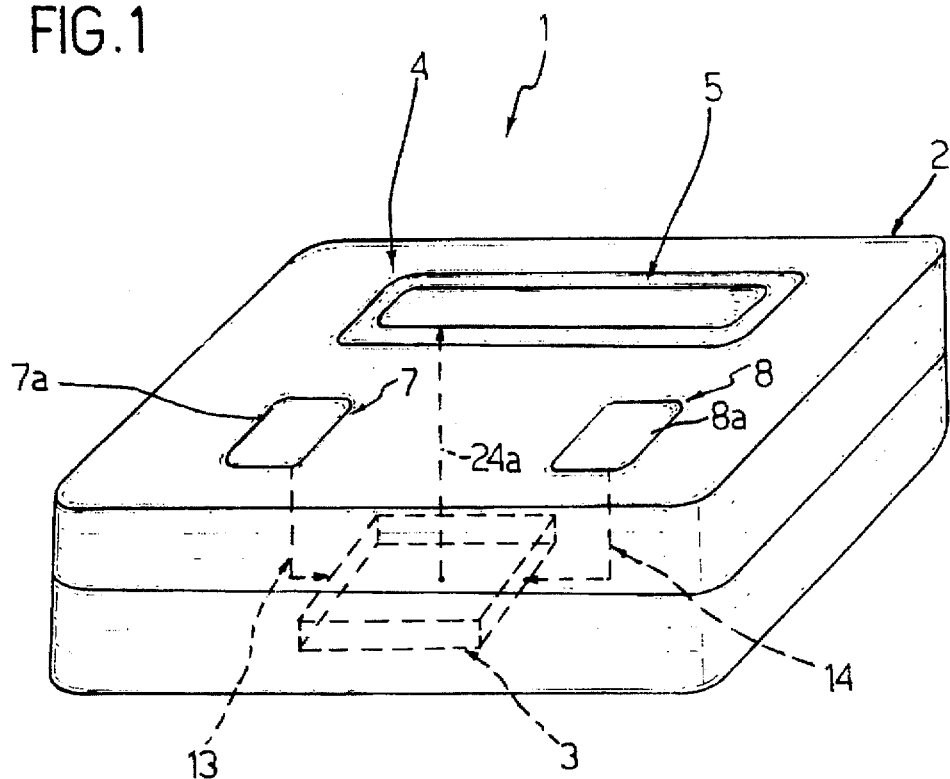
FIG. 1 shows a view in perspective of an instrument for detecting an electric biological signal, in particular an electrocardiographic signal, in accordance with the teachings of the present invention.

Number 1 in FIG. 1 indicates a pocket instrument for detecting an electrocardiographic signal, and comprising a substantially parallelepiped outer casing 2 and an electronic circuit 3 (shown schematically) housed inside casing 2.

More specifically, casing 2 presents a flat rectangular wall 4 fitted with a display 5 and with two input signal detecting electrodes 7, 8. Electrodes 7, 8 are substantially flat, comprise respective metal plates 7a, 8a on wall 4, and communicate with circuit 3 over respective electric lines 13, 14.

Figure 2:
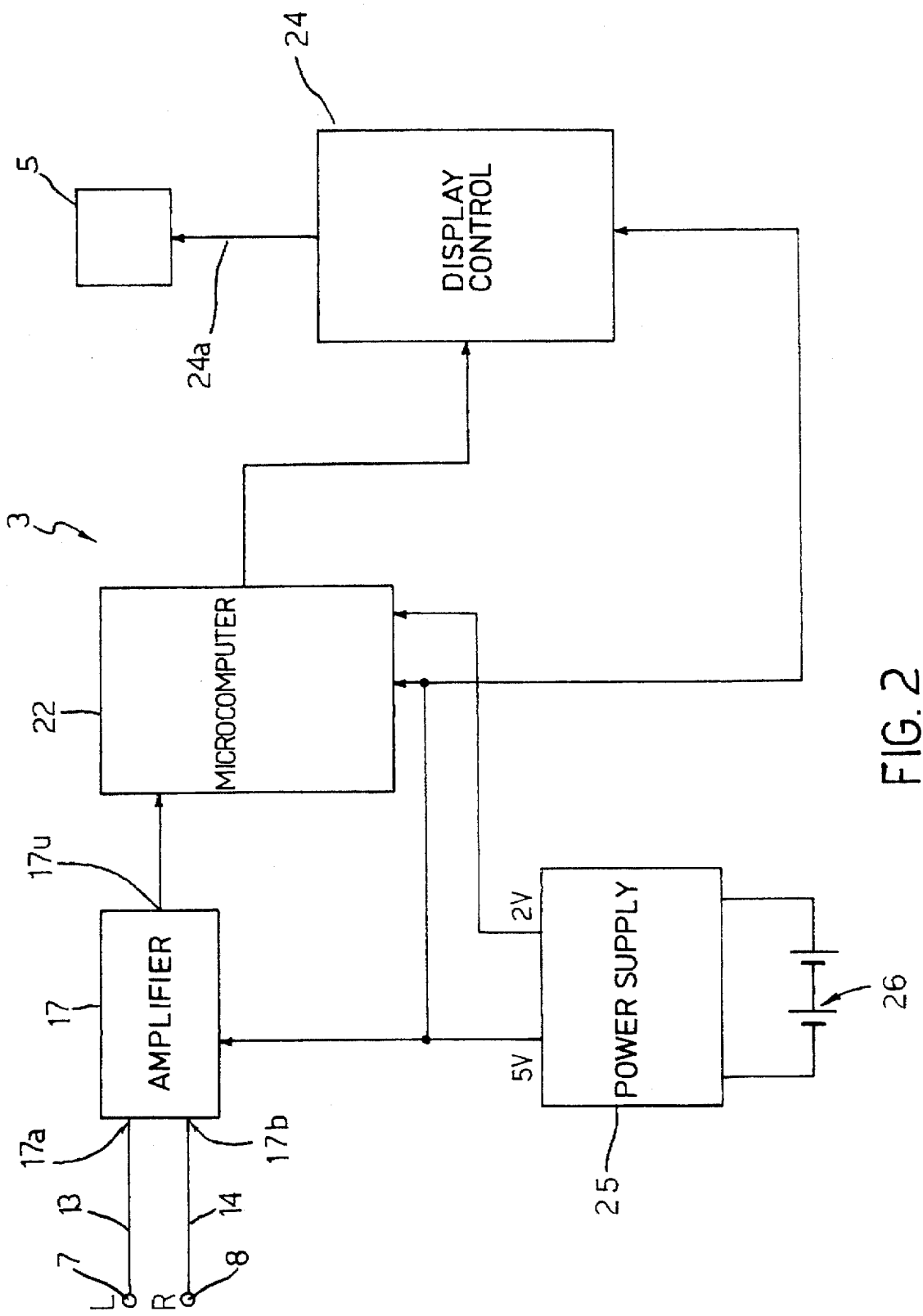
FIG. 2 shows a block diagram of the electronic circuit of the FIG. 1 instrument.

FIG. 2 shows a block diagram of electronic circuit 3 for processing the input signals. More specifically, circuit 3 comprises an amplifier 17 presenting two inputs 17a, 17b connected respectively to electrodes 7, 8 over respective electric lines 13, 14, and an output 17u connected to an input of a microcomputer 22 for processing the output signal of amplifier 17. More specifically, and as described in detail later on, amplifier 17 supplies an output signal proportional to the difference between the signals at inputs 17a, 17b.

Microcomputer 22 comprises a microcontroller (not shown); a ROM memory (not shown); a RAM data memory (not shown); and an analog/digital converter (not shown) for receiving the signals from amplifier 17.

Microcomputer 22 communicates with a drive circuit 24 for controlling display 5, which is connected to drive circuit 24 over an electric line 24a.

Circuit 3 also comprises a regulated power supply 25 supplied by one or two batteries 26 (e.g. two 1.5 V batteries in series) and communicating with amplifier 17, microcomputer 22 and drive circuit 24. More specifically, power supply 25 supplies a first 5 V voltage for supplying amplifier 17, microcomputer 22 and circuit 24; and a second 2 V voltage for supplying the data memory (not shown) of microcomputer 22 even when instrument 1 is turned off.

Figure 3:
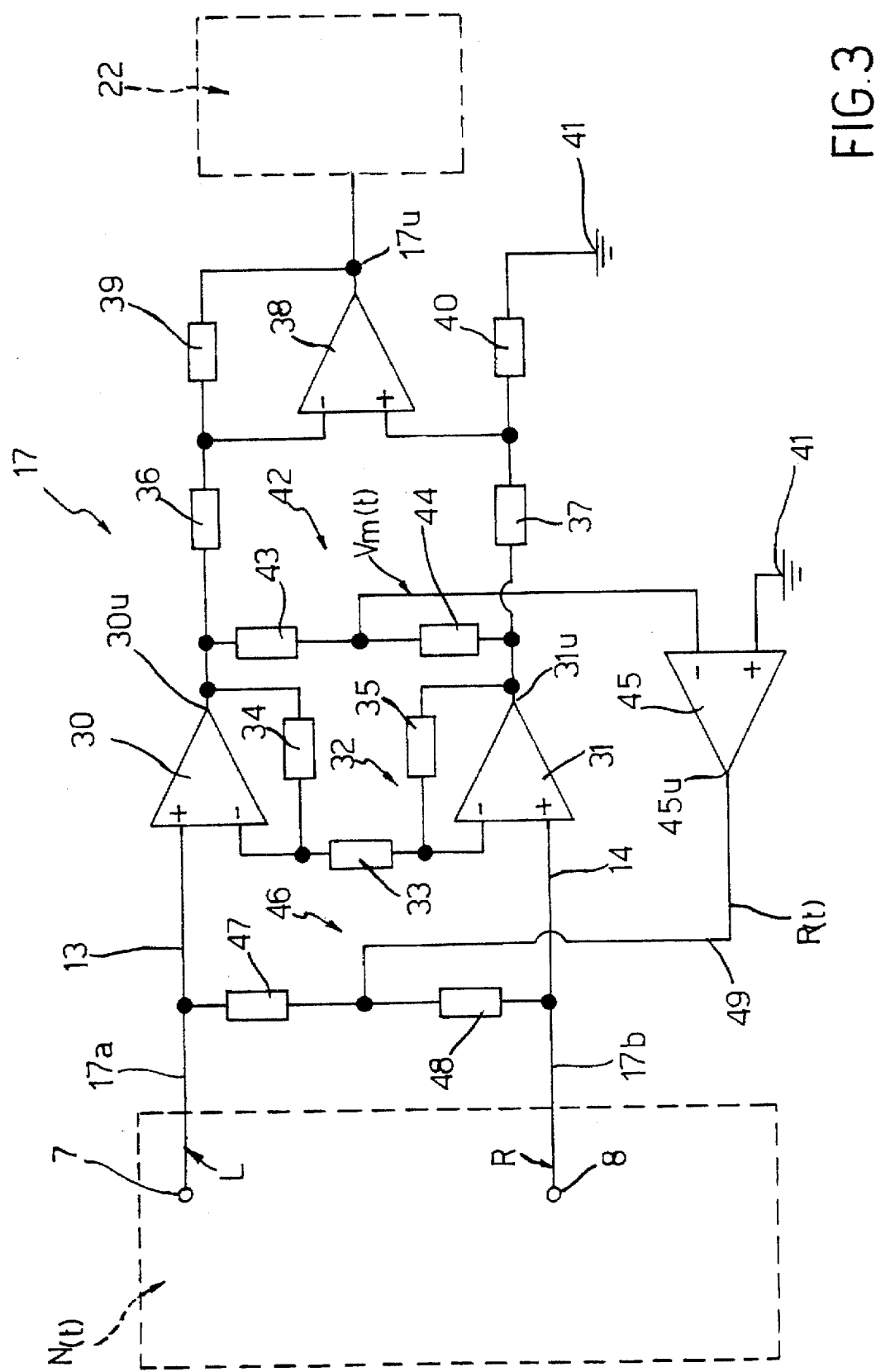
FIG. 3 shows a simplified electric diagram of an amplifier of the FIG. 2 electronic circuit.

Number 17 in FIG. 3 indicates an amplifier for amplifying an electric biological signal, and comprising a first and second operational amplifier 30 and 31 connected to each other via a resistive network 32.

More specifically, first amplifier 30 presents a noninverting input (+) connected to electric line 13, which communicates at one end with electrode 7 applied to a first portion of the body, in particular the left arm (shown schematically).

Second amplifier 31 presents a noninverting input (+) connected to electric line 14, which communicates at one end with electrode 8 applied to a second portion of the body, in particular the right arm (shown schematically).

Resistive network 32 comprises a resistor 33 between the inverting inputs (−) of amplifiers 30 and 31; a resistor 34 between the inverting input (−) and the output 30u of amplifier 30; and a resistor 35 between the inverting input (−) and the output 31u of amplifier 31; and the gain of amplifiers 30, 31 is selected (in known manner) according to the resistance of resistors 33, 34, 35.

Via respective resistors 36, 37, outputs 30u, 31u of amplifiers 30, 31 communicate respectively with the inverting input (−) and noninverting input (+) of a differential operational amplifier 38, the output 17u of which supplies a signal to microcomputer 22.

Amplifier 38 presents a biasing resistive network comprising a resistor 39 between the inverting input (−) and output 17u of amplifier 38, and a resistor 40 between the noninverting input (+) of amplifier 38 and a reference potential (ground) 41.

Amplifier 17 also comprises a resistive divider 42 located between outputs 30u and 31u, and comprising two series resistors 43, 44, the common terminals of which communicate with the inverting input (−) of an inverting amplifier 45 presenting a noninverting input (+) connected to reference potential 41.

The output 45u of inverting amplifier 45 communicates with a signal dividing circuit 46 for supplying the signal at output 45u to the first electric line 13 and second electric line 14.

More specifically, signal dividing circuit 46 comprises a resistive voltage divider formed by two series resistors 47, 48; resistor 47 presents a first terminal connected to line 13, and a second terminal connected to a first terminal of resistor 48; resistor 48 presents a second terminal connected to line 14; and the common terminals of resistors 47, 48 communicate with output 45u via an electric line 49.

Figure 4:
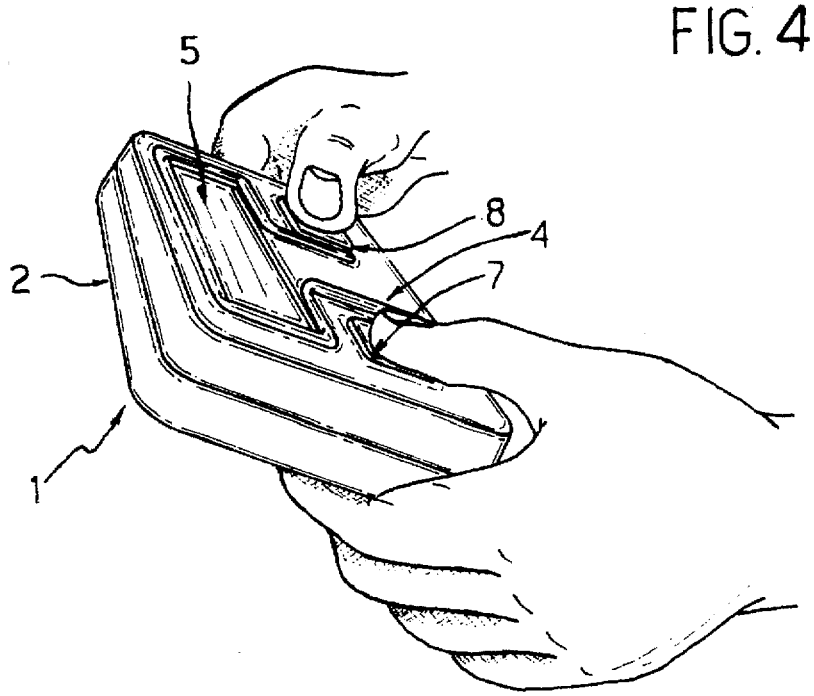
FIG. 4 shows an example of the FIG. 1 instrument in use.

In actual use (FIG. 4), the user of instrument 1 places first and second portions of the body on respective electrodes 7, 8. More specifically, the user grips outer casing 2 and places the left and right thumbs respectively on electrodes 7, 8 to electrically connect the first and second body portions to respective lines 13, 14.

Electric biological signals R and L (FIGS. 2 and 3) are thus supplied to respective amplifiers 31, 30 by which they are amplified and supplied to amplifier 38, which in turn generates an output signal proportional to the difference between the input signals, and which is supplied to microcomputer 22 for processing.

The signal supplied to microcomputer 22 is processed in known manner: microcomputer 22 memorizes and processes the input signals, and supplies display 5 with data relative to cardiac activity.

Any periodic noise signals N(t) in the body (in particular, alternating signals due to line voltage) are amplified by amplifiers 30 and 31 and supplied to divider 42 (FIG. 3).

The mid point of divider 42 therefore presents a signal Vm(t) equal to the average of the noise signals amplified by amplifiers 30 and 31; signal Vm(t) is supplied to amplifier 45, which generates a feedback signal R(t) equal to the amplified, inverted signal Vm(t); and feedback signal R(t) is supplied to signal dividing circuit 46 by which it is supplied to lines 13, 14 and added to the signals at electrodes 7, 8. Feedback signal R(t) is thus added in push-pull manner to the noise signal N(t) to eliminate (or at least attenuate) the noise signal itself.

The advantages of the present invention will be clear from the foregoing description. In particular, instrument 1, which provides for a high degree of noise rejection, requires only two electrodes, and is small enough to be carried in the pocket.

Instrument 1 is connected simply to the body with no need for electrodes external to the instrument.

Finally, instrument 1 is extremely straightforward in design and therefore cheap and easy to produce.

Clearly, changes may be made to the instrument as described and illustrated herein without, however, departing from the scope of the present invention. For example, electrodes 7, 8 may be formed in any manner, and display 5 may be replaced by or combined with printout recording systems.

I claim:

1. A pocket instrument (1) for detecting an electric biological signal, in particular an electrocardiographic signal, and comprising:

detecting means (7, 8) for detecting an electric biological signal;

amplifying means (17) for amplifying said biological signal; and processing means (3) for processing the output signal of said amplifying means (17);

characterized in that said amplifying means (17) comprise:

first amplifying means (30) presenting at least one first input (17a) communicating with a first electric line (13) connected to said detecting means (7, 8) and receiving a first electric signal (L) picked up from a first portion of a biological body;

second amplifying means (31) presenting at least one second input (17b) communicating with a second electric line (14) connected to said detecting means (7, 8) and receiving a second electric signal (R) picked up from a second portion of a biological body;

inverting amplifying means (45) receiving a signal (Vm(t)) correlated with the signal from the outputs (30u, 31u) of said first amplifying means (30) and said second amplifying means (31); and signal dividing means (46) communicating at the said first and second inputs with an output (45u) of said inverting amplifying means (45);

said signal dividing means (46) supplying the feedback signal (R(t)) at said output (45u) of said inverting amplifying means (45) to said first (13) and second (14) electric lines.

2. An instrument as claimed in claim 1, characterized in that said signal dividing means comprise voltage dividing means (46).

3. An instrument as claimed in claim 1, characterized in that said signal dividing means (46) comprise voltage dividing means including at least two bipolar dividing elements (47, 48) connected in series with each other; the opposite end terminals of said bipolar dividing elements (47, 48) communicating respectively with said first electric line (13) and said second electric line (14); and a common terminal of said bipolar dividing elements (47, 48) communicating with said output (45u) of said inverting amplifying means (45).

4. An instrument as claimed in claim 3, characterized in that said bipolar dividing elements (47, 48) comprise resistive means.

5. An instrument as claimed in claim 1, characterized by comprising differential amplifying means (38) receiving the output signal of said first and second amplifying means (30, 31), and generating at the output (17u) a signal which is supplied to said processing means (3).

6. An instrument as claimed in claim 1, characterized by comprising supporting means (2) for supporting said amplifying means (17) and said processing means (3); and by said detecting means (7, 8) comprising first and second electrodes fitted to the supporting means (2) and communicating respectively with said first electric line (13) and said second electric line (14).

7. An instrument as claimed in claim 6, characterized in that said electrodes (7, 8) are substantially flat, and comprise respective flat conducting portions (7a, 8a) incorporated in a wall (4) of said supporting means (2).

8. An instrument as claimed in claim 1, characterized by comprising display means (5) fitted to said supporting means (2) and for displaying at least one result of the processing operation performed by said processing means (3).

9. An instrument as claimed in claim 8, characterized in that said amplifying means (17) present a first and second input (17a, 17b) communicating respectively with said detecting means (7, 8), and at least one output (17u) communicating with a microcomputer (22) for memorizing and processing input signals and supplying said display means (5) with data relative to cardiac activity; said microcomputer (22) cooperating with control means (24) for controlling said display means (5).

10. A pocket instrument for detecting an electric biological signal, in particular an electrocardiographic signal, said instrument comprising:

a detector for detecting an electric biological signal;

an amplifying device for amplifying said biological signal, said amplifying device including:

a first amplifier presenting at least one first input communicating with a first electric line connected to said detector and receiving a first electric signal picked up from a first portion of a biological body;

a second amplifier presenting at least one second input communicating with a second electric line connected to said detector and receiving a second electric signal picked up from a second portion of said biological body;

an inverter receiving a signal correlated with the signal from the outputs of said first amplifier and said second amplifier;

a signal divider communicating with said first and second inputs with an output of said inverter, said signal divider supplying a feedback signal at said output of said inverter to said first and second electric lines; and processor for processing the output signal of said amplifying device.

11. An instrument as claimed in claim 10, wherein said signal divider comprises a voltage divider.

12. An instrument as claimed in claim 10, wherein said signal divider comprises a voltage divider including at least two bipolar dividing elements connected in series with each other; the opposite end terminals of said bipolar dividing elements communicating respectively with said first electric line and said second electric line; and a common terminal of said bipolar dividing elements communicating with said output of said inverter.

13. An instrument as claimed in claim 12, wherein said bipolar dividing elements comprise resistive elements.

14. An instrument as claimed in claim 10, further comprising a differential amplifier receiving the output signal of said first and second amplifiers and generating at the output a signal which is supplied to said processor.

15. An instrument as claimed in claim 10, further comprising a support for supporting said amplifying device and said processor; and by said detector comprising first and second electrodes fitted to the support and communicating respectively with said first electric line and said second electric line.

16. An instrument as claimed in claim 15, wherein said electrodes are substantially flat and comprise respective flat conducting portions incorporated in a wall of said support.

17. An instrument as claimed in claim 10, further comprising a display fitted to said support and for displaying at least one result of the processing operation performed by said processor.

18. An instrument as claimed in claim 17, wherein said amplifying device presents a first and second input communicating respectively with said detector and at least one output communicating with a microcomputer for memorizing and processing input signals and supplying said display with data relative to cardiac activity; said microcomputer cooperating with a controller for controlling said display.

* * * * *